United States Patent
Davis et al.

(10) Patent No.: US 12,167,969 B2
(45) Date of Patent: Dec. 17, 2024

(54) RESONATING IMPLANT SYSTEMS AND METHODS

(71) Applicant: NuVasive, Inc., San Diego, CA (US)

(72) Inventors: Chase Davis, San Diego, CA (US); Brijesh Poojary, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

(21) Appl. No.: 17/848,853

(22) Filed: Jun. 24, 2022

(65) Prior Publication Data

US 2023/0414365 A1 Dec. 28, 2023

(51) Int. Cl.
*A61F 2/44* (2006.01)
*A61F 2/28* (2006.01)
*A61F 2/30* (2006.01)

(52) U.S. Cl.
CPC ............... *A61F 2/447* (2013.01); *A61F 2/28* (2013.01); *A61F 2/442* (2013.01); *A61F 2002/2835* (2013.01); *A61F 2002/2864* (2013.01); *A61F 2002/30593* (2013.01); *A61F 2002/30784* (2013.01)

(58) Field of Classification Search
CPC ................... A61F 2002/286; A61F 2002/2864
See application file for complete search history.

(56) References Cited

U.S. PATENT DOCUMENTS

| | | | | |
|---|---|---|---|---|
| 4,530,360 A | * | 7/1985 | Duarte | A61H 23/0245 |
| | | | | 607/51 |
| 5,376,065 A | * | 12/1994 | McLeod | A61H 23/0218 |
| | | | | 601/100 |
| 5,730,705 A | * | 3/1998 | Talish | A61F 2/28 |
| | | | | 601/2 |
| 6,478,824 B1 | * | 11/2002 | Hagenmeyer | A61F 2/30721 |
| | | | | 623/23.15 |
| 7,833,251 B1 | | 11/2010 | Ahlgren et al. | |
| 9,044,281 B2 | | 6/2015 | Pool et al. | |
| 9,107,762 B2 | | 8/2015 | de Villiers et al. | |
| 9,180,021 B2 | | 11/2015 | Curran et al. | |
| 9,730,802 B1 | | 8/2017 | Harvey | |
| 10,179,014 B1 | | 1/2019 | Menmuir et al. | |
| 10,390,930 B2 | | 8/2019 | Arbefeuille et al. | |
| 10,675,158 B2 | | 6/2020 | Unger et al. | |

(Continued)

FOREIGN PATENT DOCUMENTS

| | | | | |
|---|---|---|---|---|
| JP | 2004154479 A | * | 6/2004 | |
| WO | WO-0028925 A2 | * | 5/2000 | ......... A61F 2/30771 |
| WO | 2021/245633 | | 12/2021 | |

OTHER PUBLICATIONS

McCarthy C, Camci-Unal G. Low Intensity Pulsed Ultrasound for Bone Tissue Engineering. Micromachines. Nov. 30, 2021; 12(12):1488. https://doi.org/10.3390/mi12121488 (Year: 2021).*

*Primary Examiner* — Julianna N Harvey
*Assistant Examiner* — Anna V. Little (57) ABSTRACT

An interbody implant to be introduced into a variety of target sites for accelerating bone ossification, for example into a space between two adjacent vertebrae. The interbody implant includes a first bone contacting surface, a second bone contacting surface, a body defined between the first and second bone contacting surfaces, and a plurality of resonators. Mechanical waves, e.g., low intensity pulsed ultrasound waves, may be transmitted to the location of the implant, causing the resonators to resonate and accelerate bone ossification.

21 Claims, 9 Drawing Sheets

(56) References Cited

U.S. PATENT DOCUMENTS

| | | | |
|---|---|---|---|
| 2003/0153849 A1* | 8/2003 | Huckle | A61N 7/00 |
| | | | 601/2 |
| 2004/0053196 A1 | 3/2004 | Mayer et al. | |
| 2009/0216113 A1* | 8/2009 | Meier | A61B 90/39 |
| | | | 600/424 |
| 2011/0112642 A1* | 5/2011 | Tohmeh | A61F 2/46 |
| | | | 623/17.11 |
| 2014/0180423 A1* | 6/2014 | Pimenta | A61F 2/4455 |
| | | | 623/17.16 |
| 2014/0277485 A1* | 9/2014 | Johnson | A61F 2/4611 |
| | | | 623/17.16 |
| 2016/0220393 A1* | 8/2016 | Slivka | A61F 2/44 |
| 2017/0027596 A1* | 2/2017 | Bonutti | A61N 7/00 |
| 2018/0250140 A1* | 9/2018 | Harvey | A61F 2/4611 |
| 2018/0280145 A1 | 10/2018 | Jones et al. | |
| 2019/0117402 A1* | 4/2019 | Stevens | A61L 27/3691 |
| 2019/0133783 A1* | 5/2019 | Unger | A61F 2/44 |
| 2019/0151192 A1* | 5/2019 | Yamashita | A61N 7/00 |
| 2020/0046512 A1 | 2/2020 | Newman et al. | |
| 2020/0375756 A1* | 12/2020 | Chevalier | A61F 2/4455 |

* cited by examiner

RESONATING IMPLANT SYSTEMS AND METHODS

TECHNICAL FIELD

The present disclosure relates generally to systems and methods for enhancing bone growth and bone healing applications, and more particularly to an implant having one or more resonators that acts as a frequency amplifier for extracorporeal signals to accelerate or otherwise amplify bone ossification and bone healing applications.

BACKGROUND

Spinal fusion procedures are commonly performed to connect two or more vertebrae in a spine, eliminating motion between them, for example to correct problems such as chronic back or neck pain. Spinal fusion procedures may include removing portions of disk(s) that are diseased or damaged and inserting one or more intervertebral implants into the resulting disc space. Spinal fusion can stop the motion between two or more vertebrae by encouraging bone to form across the defect. The bone formation process can be restrictive and time intensive.

Efforts to accelerate or otherwise improve bone formation include, for example, using Low Intensity Pulsed Ultrasound (LIPUS) technology as part of a treatment regimen. LIPUS involves transmitting low intensity and pulsed mechanical waves to a target site to induce the regenerative response in bone healing. The mechanical waves typically have a frequency of 1.5 megahertz (MHz), a pulse width of 200 microseconds (µs) repeated at 1 kilohertz (kHz), and an intensity of 30 milliwatts per centimeter squared (mW/cm$^2$). The wave generator of the LIPUS system may be positioned to contact or otherwise be in close proximity to a patient's skin near the location of the targeted bone. LIPUS treatment may occur for a prescribed schedule, such as for twenty minutes a day for a number of weeks. Because the LIPUS mechanical waves must travel through skin into soft tissue and bone to the site of an injury, the energy transported by the mechanical wave can be attenuated, thus reducing the intensity of this form of treatment relative to if the LIPUS mechanical waves were generated closer to the site of the injury. The energy of the mechanical waves can also be scattered and absorbed in tissue, further reducing its effectiveness. Despite LIPUS being a safe and effective noninvasive adjunctive therapy used to promote the bone healing process, there is still a need for improvement, especially for applications where the target fusion area is not close to the skin.

SUMMARY

The present disclosure relates to an interbody implant having resonators constructed to resonate in response to receiving mechanical waves and, in turn, promote bone ossification. The present disclosure also relates to methods of using and/or implanting the implant to promote bone ossification.

The interbody implant can be implanted where bone ossification is desired. Nonlimiting use cases of the interbody implant include implanting the interbody implant between two vertebrae where fusion is desired, between two sections of bone involved in a bone transport procedure, between two sections of bone for healing a fracture, and the like. The interbody implant is constructed to resonate in response to low intensity pulsed ultrasound (LIPUS) mechanical waves being transmitted to towards it.

The resonating of the interbody implant amplifies the LIPUS waves directed toward it, thereby increasing the intensity of the LIPUS mechanical waves closer to the site of treatment that would otherwise be attenuated, scattered or absorbed using typical non-invasive LIPUS treatment techniques. The interbody implant may be constructed to resonate in response to other types of waves as well.

The interbody implant of the present disclosure may be comprised of any suitable non-bone composition, including but not limited to titanium, titanium alloys (e.g., Ti6Al4V), polymer compositions (e.g., poly-ether-ether-ketone (PEEK) and/or poly-ether-ketone-ketone (PEKK)), ceramic, other metal, or any combination of these materials. The resonators may similarly be comprised of any suitable non-bone composition, including, but not limited to, the materials listed above.

The implant of the present disclosure may be introduced into a target site through the use of any of a variety of suitable instruments having the capability to releasably engage the implant. In an example, the insertion instrument permits quick, direct, accurate placement of the implant into the target space.

The present disclosure, in one aspect, provides a method comprising implanting an interbody implant having a plurality of resonators between adjacent vertebrae; and transmitting, by a wave generator, mechanical waves towards the interbody implant, thereby causing the plurality of resonators to resonate.

In one example, the mechanical waves comprise low intensity pulsed ultrasound waves. In an additional example, each mechanical wave has a pulse width of approximately two hundred microseconds, wherein the wave generator is configured to transmit the mechanical waves every millisecond. In yet another example, each mechanical wave has a frequency of approximately 1.5 megahertz. In another example, the method further comprises performing a treatment regimen, wherein the treatment regimen includes the transmitting; determining that ossification occurred in the space between the adjacent vertebrae, wherein the interbody implant is at least partially encapsulated by the ossification; and ceasing the treatment regimen responsive to the determining. In another example, the method further comprises packing the interbody implant with bone graft material. In an additional example, the method further comprises, prior to implanting the interbody implant, forming an incision in a patient having the adjacent vertebrae to access the space; after implanting the interbody implant, closing the incision; and wherein the transmitting occurs after closing the incision.

Another aspect of the present disclosure provides an implant, comprising: a first bone contacting surface; a second bone contacting surface; a body defined between the first and second bone contacting surfaces; and a plurality of resonators affixed to any one of (i) the first bone contacting surface, (ii) the second bone contacting surface, (iii) the body, or (iv) any combination of (i), (ii), and (iii). In an example, the resonators are constructed to resonate at a predetermined frequency. In another example, the predetermined frequency is a frequency associated with low intensity pulsed ultrasound. In an additional example, the resonators are affixed to a portion of the implant; and the resonators comprise a cylindrical shape constructed to resonate at a predetermined frequency. In another example, each resonator of the plurality of resonators comprises a first end and a second end, and wherein the resonators are affixed by any one of (i) the first end, (ii) the second end, or (iii) the first end and the second end. In another example, the implant comprises poly-ether-ether-ketone. In a further example, the implant lacks an active component. In an additional example, the first and second bone contacting surfaces are porous; and at least a portion of the porous surfaces of the first and second bone contacting surfaces are constructed to resonate at a predetermined frequency. In a further example, the implant is a total disc replacement implant. In another example, the body is porous, the porous body comprising a porous lattice structure; and the porous lattice structure is configured to resonate at a predetermined frequency. In an additional example, the body and the first and second bone contacting surfaces are porous, the porous body comprising a lattice structure, wherein the porous lattice structure and the porous surfaces of the first and second bone contacting surfaces are configured to resonate at a predetermined frequency. In another example the implant is an intervertebral implant. In yet another example, the resonators are constructed to resonate in response to receiving a mechanical wave with a frequency of approximately 1.5 megahertz; an intensity of less than 0.1 Watts per meter squared; and a pulse width of approximately two hundred microseconds.

Another aspect of the present disclosure provides a system comprising an implant selected from the group consisting of: a prosthetic disc, a spinal fusion rod, a sacroiliac joint implant, a static intervertebral implant, and an expandable intervertebral implant, wherein the implant comprises one or more resonators configured to resonate at a frequency associated with low intensity pulsed ultrasound.

BRIEF DESCRIPTION OF THE DRAWINGS

The features and advantages of the present disclosure will become more apparent from the detailed description set forth below when taken in conjunction with the following drawings. Throughout the several figures and examples, like components are referred to by like reference numbers unless otherwise indicated.

DETAILED DESCRIPTION

Resonating Interbody Implant

Traditionally, LIPUS is used to aid bone healing in bones that are very close to the surface of the skin (e.g., tibial, radial, or ulnar fractures) where LIPUS waves are less attenuated by tissue. By contrast, deep bone growth locations (e.g., intervertebral space) presents challenges in effective treatment with LIPUS. The disclosed examples herein include the use of resonating implants or components of implants to address one or more of these challenges.

The examples presented herein are directed to systems and methods for enhancing bone growth and bone healing applications, and more particularly to a resonating interbody implant that is constructed to operate as an amplifier to accelerate or otherwise amplify bone ossification and bone healing applications.

A resonator is an apparatus, device or system that exhibits resonance or resonant behavior. A resonator naturally oscillates with greater amplitude at some frequencies, called resonant frequencies, than at other frequencies. The oscillations in a resonator can be either electromagnetic or mechanical. In the example embodiments described herein, the oscillations are mechanical.

In an example embodiment, the implant includes a first bone contacting surface, a second bone contacting surface a body defined between the first and second bone contacting surfaces, and one or more resonators. The one or more resonators resonate in response to mechanical waves and cause the implant to vibrate, thereby accelerating bone ossification by amplifying the mechanical waves. The vibration of the implant can accelerate bone ossification by, for example, inducing micromechanical stress to the bone and/or stimulation of one or more molecular and cellular responses involved in bone ossification. The resonant vibration can be conducted to areas near the implant and encourage bone growth nearby or within the implant (e.g., bony ingrowth or ongrowth).

Figure 1:
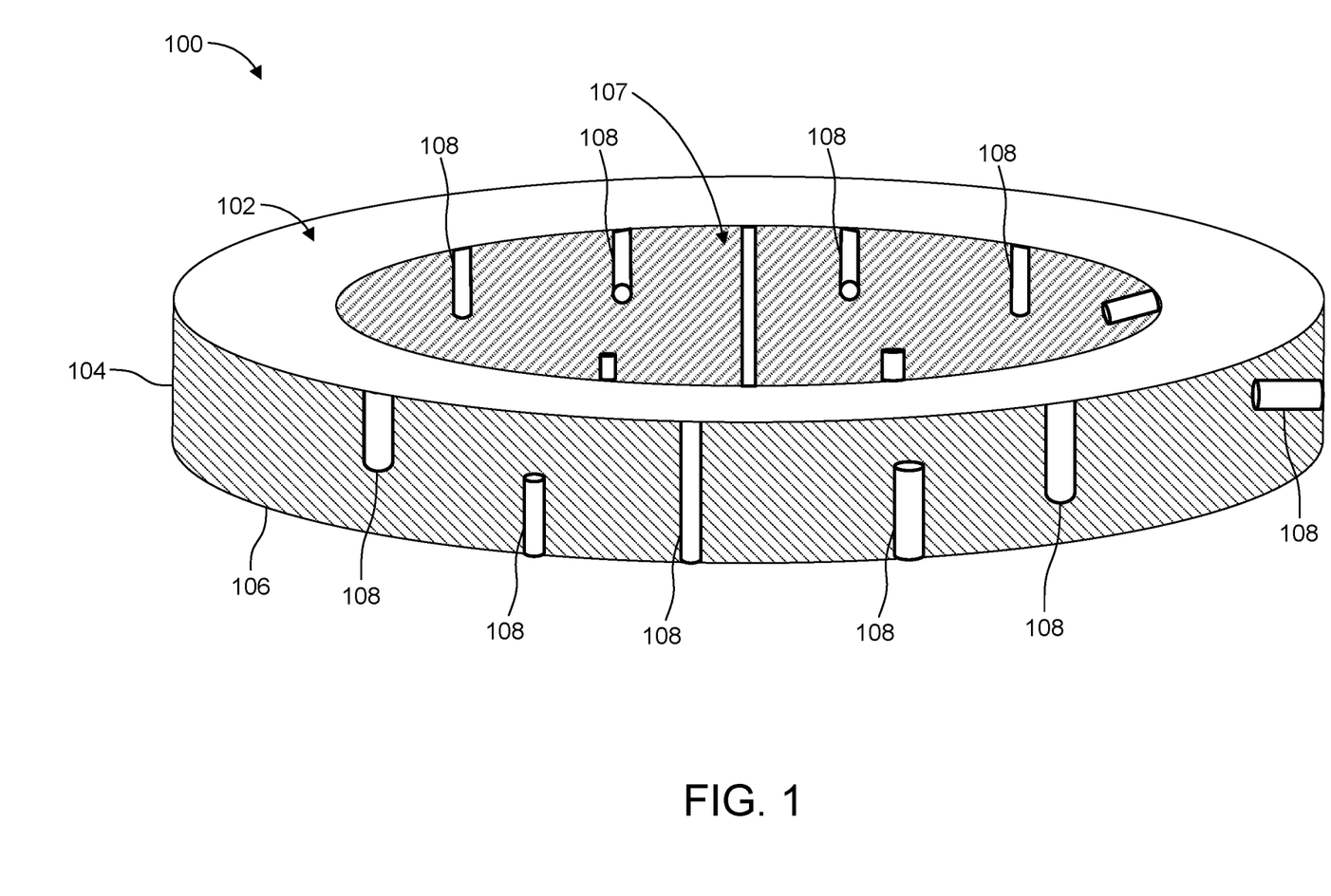
FIG. 1 illustrates an implant with various resonators in accordance with examples of the present disclosure.

FIG. 1 illustrates an implant with various resonators in accordance with examples of the present disclosure. The implant 100 shown in FIG. 1 may be constructed to be sized and/or shaped for any useful application. For example, the implant 100 can take a variety of forms, such as joint replacement implants (e.g., hip replacement, knee replacement, or shoulder replacement), fracture healing implants (e.g., plates, rods, screws, or nails), bone transport systems (e.g., growing rods), spinal fusion implants (e.g., expandable or static intervertebral implants designed for use with spinal fusion procedures, such as anterior, lateral, posterior, or transforaminal approaches), other implants, or combinations thereof. In the illustrated example, the implant 100 is sized and shaped to be implanted between two adjacent vertebrae for use in a fusion procedure.

As illustrated in FIG. 1, the implant 100 has a first bone contacting surface 102, a body 104, a second bone contacting surface 106 (not shown due to the orientation), and multiple resonators 108. The implant 100 further defines an aperture 107. The implant 100 may be sized and shaped such that the implant 100 may be implanted between two vertebrae so the first bone contacting surface 102 contacts or otherwise engages with one of the vertebrae (e.g., a superior vertebra) and the second bone contacting surface 106 contacts or otherwise engages with the other vertebra (e.g., an inferior vertebra).

In the illustrated example, the implant 100 defines an aperture 107 extending vertically between the first and second bone contacting surfaces 102, 106. The aperture 107 can be provided in any number of suitable shapes, such as circular, triangular, or oblong. The aperture 107 is a feature for promoting fusion between upper and lower vertebral bodies which allow a boney bridge to form through the implant 100 to achieve fusion. Fusion may be facilitated or augmented by including bone growth material(s) within the aperture 107 and/or adjacent to the spinal fusion implant 100. Such materials may be introduced before, during, or after insertion of the implant 100, and may include autologous bone harvested from the patient receiving the implant 100, bone allograft, bone xenograft, any number of non-bone implants (e.g. ceramic, metallic, polymer), bone morphogenic protein, and bio-resorbable compositions, other materials, or combinations thereof.

The first bone contacting surface 102, the body 104, and/or the second bone contacting surface 106 may be constructed to be solid and/or porous. If the first bone contacting surface 102, the body 104, and/or the second bone contacting surface 106 are constructed to be solid, the resonators 108 may be embedded in the solid portion(s) of the implant 100. In this illustration, certain resonators 108 are attached only to the first bone contacting surface 102, certain resonators 108 are attached only to the second bone contacting surface 106, certain resonators 108 are attached to both the first bone contacting surface 102 and the second bone contacting surface 106, and certain resonators 108 are attached to the body 104. The resonators 108 may be positioned differently in other examples. The resonating capabilities of the resonators can be location independent because the resonators 108 will resonate in response to a transmitted mechanical wave (e.g., a LIPUS wave) at any position in the implant. Thus, the resonators 108 can be affixed anywhere on the implant 100 without compromising the resonating effects of the resonators 108. In this illustration, the resonators 108 are rods, and the resonators 108 may be constructed according to equations 1, 2, 3, and/or 4 below to resonate at a desired frequency, for example at the 1.5 MHz frequency of a LIPUS wave.

Any number of resonators 108 may be affixed to the implant's 100 (i) first bone contacting surface, (ii) second bone contacting surface, (iii) body, or (iv) any combination of (i), (ii), and (iii) as desired and/or needed.

The implant 100 may be implanted such that the first bone contacting surface 102 contacts a first bone surface and/or the second bone contacting surface 106 contacts a second bone surface. For example, the implant 100 may be implanted between two adjacent vertebrae with the first bone contacting surface 102 contacting one vertebrae and the second bone contacting surface 106 contacting the other vertebrae. The implant 100 may resonate in response to the transmission of mechanical waves to the position between the adjacent vertebrae and accelerate bone ossification between the two vertebrae.

In some examples, the implant 100 includes an active component (e.g., a piezoelectric generator or a motor) to cause the resonators 108 to resonate. In other examples, the implant 100 lacks such an active component. In some examples, the implant 100 has one or more internally or externally powered circuits. The resonators 108 can be associated with such circuits, such that the resonating of the resonators 108 can be sensed (e.g., via an implanted piezoelectric sensor). The sensed resonating can be used to determine whether resonance has been achieved. The sensed resonating can be communicated to an external treatment device for tuning or controlling treatment. In other examples, the implant 100 can lack an active component. Or where the implant 100 lacks such an active component, resonators 108 can be separate from such circuits. For instance, the active components can operate without respect to the vibrations of some or all of the resonators 108. The other resonators described herein may also include one or more of the active components described.

In an example embodiment, the resonators are affixed to any one of (i) the first bone contacting surface, (ii) the second bone contacting surface, (iii) the body, or (iv) any combination of (i), (ii), and (iii). The first (i) the first bone contacting surface, (ii) the second bone contacting surface, (iii) the body, or (iv) any combination of (i), (ii), and (iii) may have a structure (e.g., a lattice) that are the one or more resonators. Thus, resonators may also be components of the implant, including (i) the first bone contacting surface, (ii) the second bone contacting surface, (iii) the body, or (iv) any combination of (i), (ii), and (iii) for example. As used herein, a resonator refers to a resonating feature of an implant, including a resonator that is not part of the structure of the implant and/or a resonator that is part of the structure of the implant (e.g., porous bone contacting surfaces of the implant, a porous body of the implant, structural portions of the implant, or the like). In the example implementations described herein, the implants include plural resonators, but the implants may include a single resonator in other implementations.

In some examples, the resonators 108 are affixed to an implant in a position to avoid direct contact between the resonators and bone. In an example implementation, the resonators 108 are affixed in the interior of the implant and/or embedded in portions of the implant. In some examples, the resonators 108 extend into the aperture 107. The resonators 108 can be disposed such that the resonators 108 would be in contact with bone growth material used with the implant 100. In other example implementations, the resonators 108 are affixed to the implant in a position that positions the resonators in direct contact bone. For example, the resonators are formed as spikes constructed to contact the bone. Resonators that are in in direct contact with bone, such as resonators in the form of spikes, can also provide stability to the implant and resist the implant from migrating.

The resonators 108 may be constructed to resonate at a predetermined frequency. The predetermined frequency can be a frequency selected to encourage bone growth, healing, or other beneficial effects. For example, the resonators 108 may be constructed to resonate at a frequency of approximately 1.5 MHz. Thus, the resonators will resonate when the resonators receive a mechanical wave that has a frequency of approximately 1.5 MHz (e.g., a low intensity pulsed ultrasound (LIPUS) wave). The resonators may cause the other portions of the implant to resonate or otherwise vibrate when the resonators resonate, thereby accelerating bone ossification by amplifying the effects of the mechanical wave. Advantageously, the resonators can be controlled by causing mechanical waves with the predetermined frequency to be transmitted to the implant.

The implant can include multiple resonators 108 that vibrate at different frequencies. For example, a first group of resonators attached to the first bone contacting surface and/or the second bone contacting surface may resonate at a first frequency, and a second group of resonators attached to the body may resonate at a second frequency. Thus, transmitting mechanical waves that have the first frequency to the implant will cause the first group of resonators will resonate. Similarly, transmitting waves that have the second frequency to the implant will cause the second group of resonators will resonate. Thus, the implant may resonate at different frequencies when multiple resonators that have different resonating frequencies are affixed or otherwise included in the implant. Additionally, isolating the resonation of the resonators attached to the first bone contacting surface and/or the second bone contacting surface can accelerate bone ossification for at least initial stability and/or ossification of the bone. Isolating the resonation of the resonators attached to the body can accelerate bone ossification for at least long-term stability and/or ossification of the bone. In another example, the resonators may resonate at the same frequency, and a uniform distribution of ossification occurs throughout the implant.

The implant, including the resonators, may be comprised of any suitable non-bone composition, including but not limited to titanium, titanium alloys (e.g., Ti6Al4V), polymer compositions (e.g., poly-ether-ether-ketone (PEEK) and/or poly-ether-ketone-ketone (PEKK)), ceramic, other metal, or any combination of these materials. The material can be chosen to construct the resonators to resonate at a desired frequency.

Resonators

In an example, the resonators 108 have a cylindrical shape. For example, the resonators may be rods affixed to the implant at either one of the rod's ends or at both of the rod's ends at any of the implant's (i) first bone contacting surface, (ii) second bone contacting surface, (iii) body, (iv) other features, or (v) any combination of (i), (ii), (iii), and (iv). The rods can be constructed to have a predetermined resonating frequency, for example according to the following equations. Table 1 below provides a summary of symbols used in describing the example embodiments.

TABLE 1

| Symbol | Meaning |
| --- | --- |
| L | Length of the rod |
| V | Speed of sound in the material of the rod |
| f | Frequency |
| N | Harmonic |
| d | Diameter |

The rod may be constructed based on the speed of sound, V, of the material the resonator is made of. For example, the speed of sound, V, in the titanium alloy Ti6Al4V is approximately 5,000 m/s.

For a rod affixed at both ends and with L>>d, determining the required length of the rod to resonate at a predetermined frequency includes applying equation 1 below:

$$L = \frac{V}{2f} * N \quad (1)$$

For example, when constructing the rods to resonate at a frequency of 1.5 MHz (e.g., the frequency of a LIPUS wave) and with the material Ti6Al4V, equation 1 can be used to determine the required length of the rod:

$$L = \frac{5,000}{2 * 1,500,000} * N$$

Therefore, for N=1, L=1.67 mm; for N=2, L=3.33 mm; for N=3, L=5 mm; and so on. T Constructing the rods can at any of these lengths when using Ti6Al4V causes the rods to resonate when the rods receive a mechanical wave with a frequency of 1.5 MHz, such as a LIPUS wave. Altering the length of the rods and/or the material can cause the rods to resonate at a different frequency as desired.

For a rod affixed at both ends and with L not >>d, determining the required length of the rod to resonate at a predetermined frequency includes applying equation 2 below:

$$L + 0.8d = \frac{V}{2f} * N \quad (2)$$

Thus, the diameter of the rod affects the available lengths for a rod to have a desired resonating frequency in this example. Modifying the length, diameter, and/or material of the rods can cause the rod to resonate at any desired frequency. In an example, a rod is affixed to the implant at one end and contacts bone at the second end. The rod may be constructed according to equation 1 or 2 in this example.

For a rod affixed at one end and with L>>d, determining the required length of the rod to resonate at a predetermined frequency includes applying equation 3 below:

$$L = \frac{V}{4f} * (2N - 1) \quad (3)$$

For example, when constructing the rods affixed at one end to resonate at a frequency of 1.5 MHz (e.g., the frequency of a LIPUS wave) and with the material Ti6Al4V, equation 3 can be used to determine the required length of the rod:

$$L = \frac{5,000}{4 * 1,500,000} * (2N - 1)$$

Therefore, for N=1, L=0.83 mm; for N=2, L=2.5 mm; for N=3, L=4.17 mm; and so on. Constructing the rods can at any of these lengths when using Ti6Al4V causes the rods to resonate when the rods receive a mechanical wave with a frequency of 1.5 MHz, such as a LIPUS wave. Altering the length of the rods and/or the material can cause the rods to resonate at a different frequency as desired.

For a rod affixed at one end and with L not >>d, determining the required length of the rod to resonate at a predetermined frequency includes applying equation 4 below:

$$L + 0.4d = \frac{V}{4f} * (2N - 1) \quad (4)$$

Thus, the diameter of the rod affects the available lengths for a rod to have a desired resonating frequency in this example. Modifying the length, diameter, and/or material of the rods can cause the rod to resonate at any desired frequency. Thus, while the above discussion primarily related to Ti6Al4V and LIPUS waves, it will be understood that other materials and/or waves can be used.

Referring again to FIG. 1, the size of the resonators 108 may be smaller and/or larger than shown. For example, as calculated above, a cylindrical resonator constructed to have a resonating frequency at 1.5 MHz and made of Ti6Al4V can be as small as 0.83 mm in length, with a smaller diameter than the length. Thus, hundreds and up to thousands of resonators 108 can be affixed to the implant 100 when the implant 100 is sized to be implanted between, for example, adjacent vertebrae.

The implants described herein may include differently shaped resonators. For example, the resonators may be a sheet, a prism, a sphere, a cone, a coil, and the like. Additionally, the resonators may include multiple shapes, such as a cylinder with a spherical end for example. Each possible shape may have associated equations to determine the necessary dimensions of the resonators for the resonators resonate at a desired frequency, similar to equations 1, 2, 3, and 4 associated with a resonator having a cylindrical shape. Therefore, while cylindrical resonators are shown in FIGS. 1, 2, 3A, 4A, and 4B, the resonators may be any shape in additional examples.

The resonators may be shaped to be arranged in the implant. The required dimensions of a certain shape of a resonator may prevent some shapes from fitting in a certain resonator, so the shapes of the resonators may differ based on the construction of the resonator. For example, The resonator may include a substantially cylindrical space. A cylindrical resonator may be used for the resonator because the cylindrical resonator will fit in the substantially cylindrical space. In another example, a resonator has a substantially rectangular space. A resonator shaped as a rectangular prism may fit in the rectangular space and therefore be used in the resonator.

In some examples, the resonators are dedicated resonant features added to an implant (e.g., the resonators 108 are not configured to substantially contribute to the stability or structural support of the implant 100). In other examples, features of the implants can be designed to function as resonators in addition to the traditional function of the feature. For instance, porous features of the implant, struts, apertures, and/or other features of the implant can be made to function as resonators. Designing the required structure of the differently shaped resonators may include using computational modeling such that the resonators have the desired resonant frequency.

The resonating implants of the present disclosure may be constructed in any form that is now known or will be known in the future for use in medical applications. Example implants that may benefit from techniques described herein include those related to bone ossification, including one or more surgical implants described by U.S. Pat. No. 10,675,158 (application Ser. No. 16/010,405, filed Jun. 16, 2018); U.S. Pat. No. 10,390,960 (application Ser. No. 15/635,087, filed Jun. 27, 2017); U.S. Pat. No. 9,730,802 (application Ser. No. 14/597,085, filed Jan. 14, 2015); and U.S. Pat. No. 9,180,021 (application Ser. No. 14/314,823, filed Jun. 25, 2014), the contents of which are incorporated by reference herein in their entirety for any and all purposes. For example, resonators can be affixed to existing implants or implants that will be used in the future, thereby allowing the implant to resonate in response to transmitted mechanical waves such as a LIPUS wave. Additionally, the components of the implant (e.g., bone contacting surfaces, the body, a fixation element, or the like) may be configured to be resonators by constructing the components to have a desired resonate frequency.

The resonating implant may be implanted for spinal fusion, bone fracture healing, bone transport, and/or any other application related to bone ossification. FIGS. 1, 2, 3A, 3B, 4A, and 4B illustrate example resonating implants. The resonating implant of the present disclosure may include additional examples that are not shown, including for example an expandable implant, a differently shaped implant, an implant used for bone transport, an implant for other bone ossification applications, or the like. For example, the following description may apply to spinal fusion implant devices shaped to be implanted into the spine via any known surgical approach to the intervertebral disc space (e.g., direct lateral, anterolateral, anterior, or posterior). Resonators may be affixed to the spinal fusion implant devices and/or the spinal fusion implant devices may be constructed so that one or more components of the devices resonate. In another example, the following description may apply to bone transport devices shaped to be implanted into bones via any known surgical approach, including the bone transport system described by U.S. Pat. No. 9,044,281 (application Ser. No. 13/655,246, filed Oct. 18, 2012), which is incorporated by reference herein. Resonators may be affixed to the bone transport system and/or the bone transport system may be constructed so that at least a portion of the system resonates.

Implant Construction

The resonating interbody implants may be constructed using any known or future known method, including machining, molding, three dimensional (3D) printing, other methods, or combinations thereof. For example, the implant may be 3D printed using a single material or using multiple materials, such as one material for the body and another material for the resonators. The resonators of the implant may be affixed to the implant as part of the printing process, integrating the resonators into the implant. In other examples, the implant will be 3D printed according to sizes, shapes, configurations, or the like that allow one or more components of the implant to be the resonator of the implant. In an example, the implant includes resonators that are rods and resonators that are components of the implant.

In another example, the implant may be machined. For example, the material used to construct the implant may be PEEK, and the resonators of the implant may be constructed of Ti6Al4V. The machining process can include affixing the resonators to the surface of the implant and/or embedding the resonators in the implant. The resonators may be affixed using adhesive, placed in machined apertures, or the like. The resonators may be embedded in the implant in apertures and subsequently covered, material can be placed around the resonators (e.g., the resonators are placed in a mold that is then filled with the material to construct the implant), or the like.

The position of the resonators can be determined using computational modeling. The placement of the resonators can be based on stability, protecting the resonators, preventing the resonators from interfering with other components of the implant, or the like. For example, the resonators may be positioned in the body of the implant in sites that protect the resonators from damage during implantation of the implant and/or prevent the resonators from interfering with components such as the bone contacting surfaces.

Treatment

Bone ossification treatment regimens utilizing the example resonating implants described herein can include using LIPUS technology. In some example implementation, a target site is a location at which a resonating implant is positioned. In some example implantations, a target site is a location based on where bone growth is desired and where the resonating implant is located. Using a LIPUS system in conjunction with a resonating implant according to the embodiments described herein to transmit low intensity and pulsed mechanical waves to a target site as part of a treatment regimen involving bone ossification may accelerate or otherwise improve the bone ossification at the target site. In an example treatment regiment, the LIPUS system is configured to transmit mechanical waves that typically have a frequency of 1.5 megahertz (MHz), a pulse width of 200 microseconds (μs) repeated at 1 kilohertz (kHz), and an intensity of 30 milliwatts per centimeter squared (mW/cm$^2$). It should be understood that the frequency, the pulse width, the time between pulses, and/or the intensity of the transmitted LIPUS waves may be different in other examples and still be within the scope of the embodiments described herein. The wave generator (e.g., a transducer) of the LIPUS system may be positioned to contact or otherwise be in close proximity to the patient's skin near the location of the targeted bone. For example, for a fusion treatment, the wave generator may contact the skin at the relative external location of a vertebral disc for treating a fusion of two vertebrae. In another example, for a tibial fracture treatment, the wave generator may contact the skin at the patient's shin for treating a tibial fracture. The wave generator can transmit LIPUS waves to the location of the targeted bone, thereby causing the resonating implant to resonate and accelerate and/or otherwise enhance bone ossification. A LIPUS treatment regimen may include LIPUS treatment sessions incorporating use of the resonating implant for a prescribed schedule, such as for twenty minutes a day for a number of weeks while the bone ossifies.

The interbody implant can be implanted in a position where bone ossification is desired (e.g., between two vertebrae where fusion is desired, between two sections of bone for a bone transport technique, between two sections of bone for healing a fracture), and the interbody implant can resonate in response to the LIPUS mechanical waves being transmitted to the position. The resonating of the interbody implant accelerates or otherwise promotes bone ossification. For example, the resonating of the interbody implant amplifies the LIPUS waves and thereby amplifies the bone ossification effects of the LIPUS waves. The interbody implant may also be constructed to resonate in response to other types of waves.

Alternative Example Resonating Interbody Implants

Figure 2:
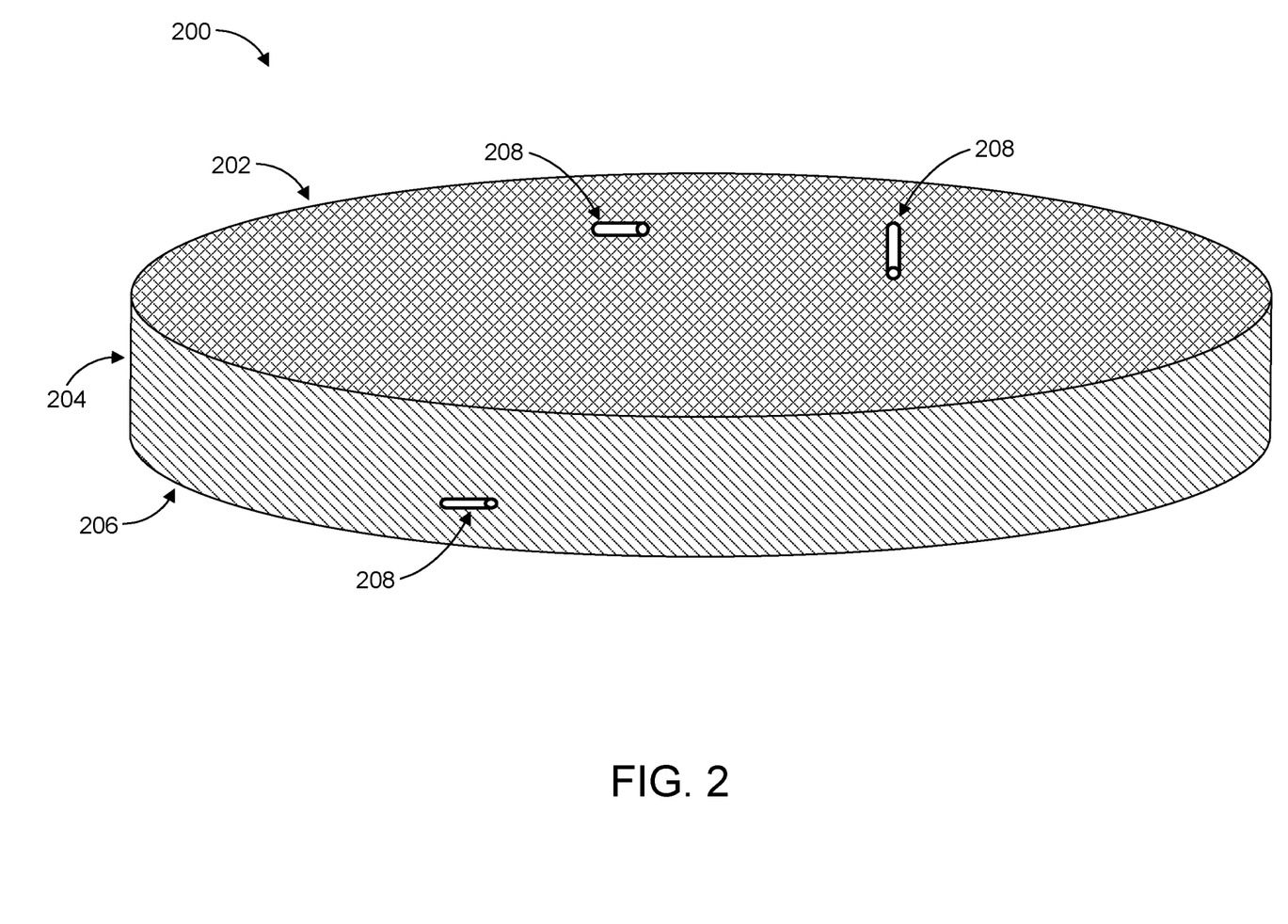
FIG. 2 illustrates an implant with various resonators in accordance with examples of the present disclosure.

FIG. 2 illustrates another example implant with various resonators in accordance with the present disclosure. FIG. 2 illustrates the implant 200 where the first bone contacting surface 202, the body 204, and the second bone contacting surface 206 (not shown due to the orientation) have porous lattice structures. The porous lattice structures of the first bone contacting surface 202, the body 204, and/or the second bone contacting surface 206 may be constructed to resonate at a predetermined frequency. For example, one or more struts of the lattice structure may have a diameter, length, material, and/or configured for the porous lattice structure or portions thereof to resonate at a specific frequency, for example the frequency of a LIPUS wave.

The implant 200 may also include resonators 208 that are affixed to the lattice structures of the first bone contacting surface 202, the body 204, and/or the second bone contacting surface 206. In this example, the lattice structures are substantially uniform. The lattice structure and/or the resonators may be constructed to resonate at the desired frequency, allowing the implant 200 to accelerate bone ossification. For example, the uniform lattice consists of struts that are sized and made of a material that causes the uniform lattice to resonate at the desired frequency. In some examples, the resonators 208 are integral with struts of the implant 200. The resonators can be branch-like structures extending from one or more struts.

Figure 3A:
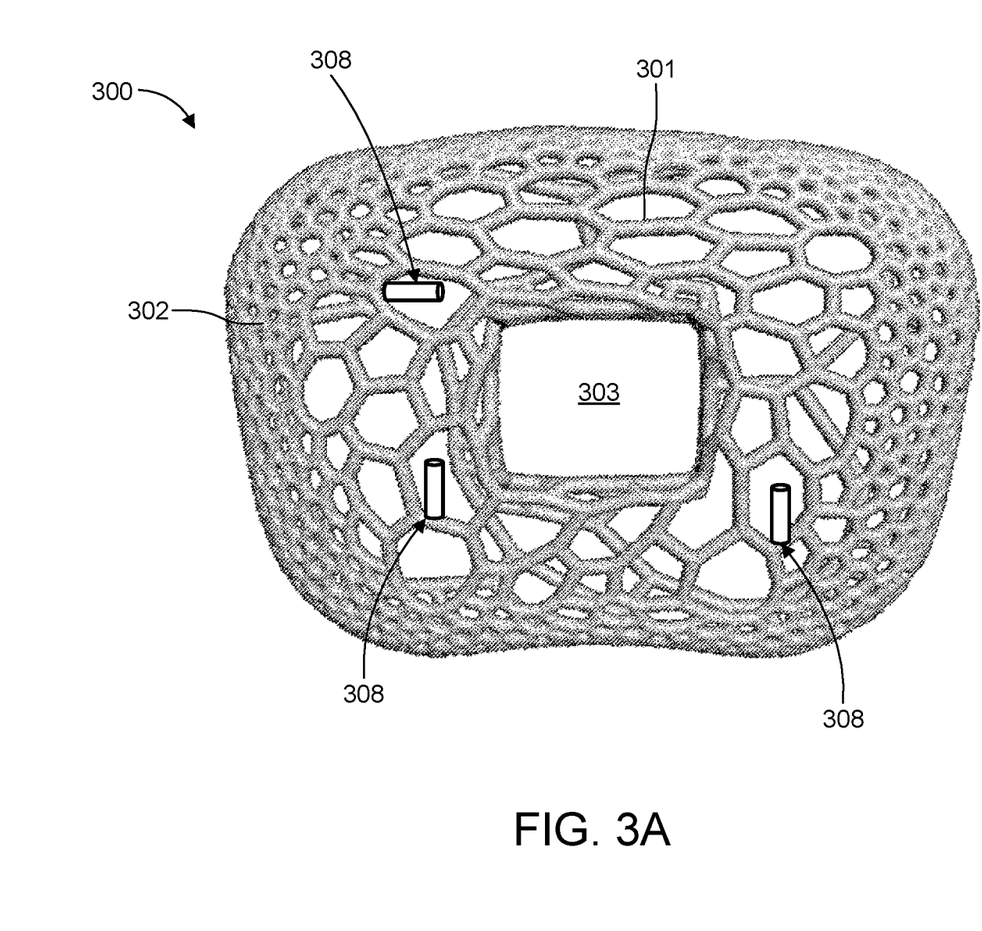
FIG. 3A illustrates a view of an example structure of the implant with a porous structure in accordance with examples of the present disclosure.
Figure 3B:
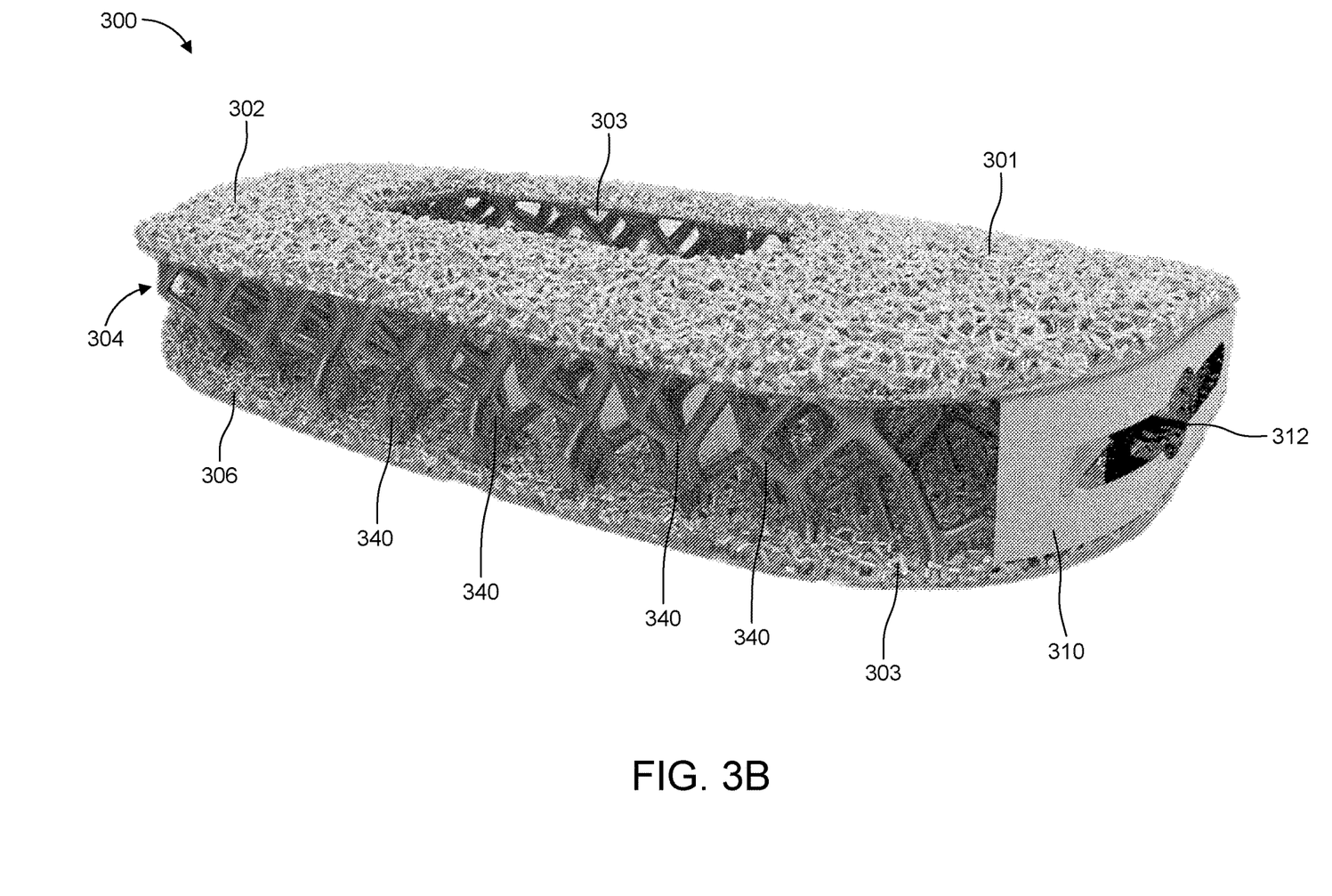
FIG. 3B illustrates another view of the example structure of the implant with a porous structure depicted in FIG. 3A and in accordance with examples of the present disclosure.

FIGS. 3A and 3B illustrate two views of another example structure of the implant with a porous structure in accordance with examples of the present disclosure. The implant 300 illustrated in FIGS. 3A and 3B include porous structures defined by struts. The struts may be resonators in these examples and/or resonators may be affixed to the implant 300.

FIG. 3A illustrates a top perspective view of the implant 300 having a porous structure. The first bone contacting surface 302 is visible in FIG. 3B. The first bone contacting surface 302 consists of a porous lattice structure 301 and the implant 300 also includes resonators 308 and a fusion aperture 303. The fusion aperture 303 extends through the implant from the first bone contacting surface 302 to the second bone contacting surface 306 (not shown in FIG. 3A). The fusion aperture 303 may function as an avenue for bone ossification. Thus, bone ossification may be direct (through the fusion aperture 303) and indirect (through the porous lattice structure 301 of the implant 300). In some examples, the fusion aperture 303 is not included and the porous lattice structure 301 is continuous.

The porous lattice structure 301 comprises a network of struts, and the arrangement of the struts defines the size and shape of the pores of the porous lattice structure 301. The struts of the porous lattice structure 301 may have a diameter, length, material, and/or structure that allows the porous lattice structure to resonate at a specific frequency, for example the frequency of a LIPUS wave. Thus, the porous lattice structure 301 would be the resonator of the implant 300. In the illustrated example, the struts and the pores created therefrom are non-uniformly shaped. The porous lattice structure 301 may be shaped to have an elastic modulus that matches or is in the same range as a patient's own bone to better conform to the bone. Thus, the improved contact will further accelerate or otherwise improve bone ossification when the implant 300 resonates.

Additionally, the implant may include resonators 308 attached to the porous lattice structure 301. Three resonators 308 are shown in the illustrated example, but any number of resonators 308 can be attached to the porous lattice structure in other examples. The resonators 308 are cylindrical in this example, but the resonators 308 may be different shapes in other examples. The implant 300 may include resonators 308 and/or a resonant porous lattice structure 301 as desired for accelerating bone ossification.

FIG. 3B illustrates a side perspective view of the implant 300. The first bone contacting surface 302 and the second bone contacting surface 306 comprise the porous lattice structure 301. In this example, the porous lattice structures 301 of the first bone contacting surface 302 and the second bone contacting surface 306 are substantially the same, but the porous lattice structures 301 of the first bone contacting surface 302 and the second bone contacting surface 306 may differ in further examples. The body 304 comprises struts 340 that create a porous body structure. Similar to the porous lattice structure 301, the struts may be constructed to resonate at a predetermined frequency, for example by constructing the struts 340 to have a diameter, length, material, and/or structure that causes the struts 340 to resonate at the desired frequency. In some examples, there are no cylindrical resonators 308. When including cylindrical resonators, the porous lattice structure 301 and/or the struts 340 may not have resonating properties. In further examples, resonators may be embedded or otherwise fixed in the lattice structure 301 of the first bone contacting surface 302 and/or the second bone contacting surface 306 and/or the struts 340, such as the resonators 308.

The implant 300 may additionally include an instrument engagement feature 310 that has at least one engagement portion 312 for the engagement of an insert tool. According to one example, the instrument engagement feature 310 includes a portion configured to receive at least a portion of a fixation element, such as a fixation plate, a fixation tab, or a bone screw. In an example, the fixation element may be constructed to resonate at a predetermined frequency, thereby amplifying the effects of mechanical waves transmitted to the location of the implant 300. The engagement feature 310 and the engagement portion 312 may be used to implant the implant 300 at a desired location, such as between vertebrae. The engagement feature 310 and the engagement portion 312 may be incorporated into the other examples herein.

Figure 4A:
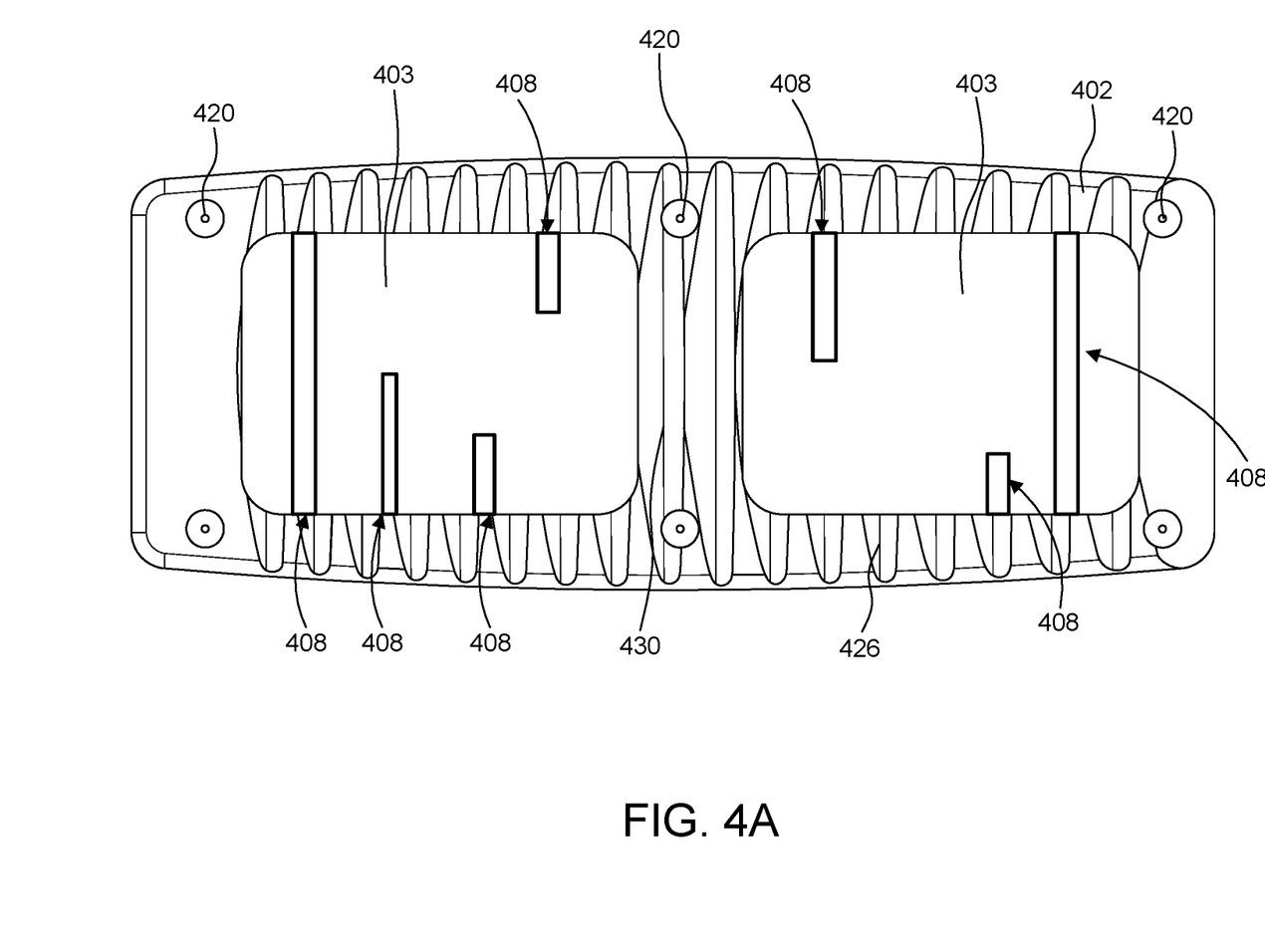
FIG. 4A illustrates a view of a further example structure of the implant in accordance with examples of the present disclosure.
Figure 4B:
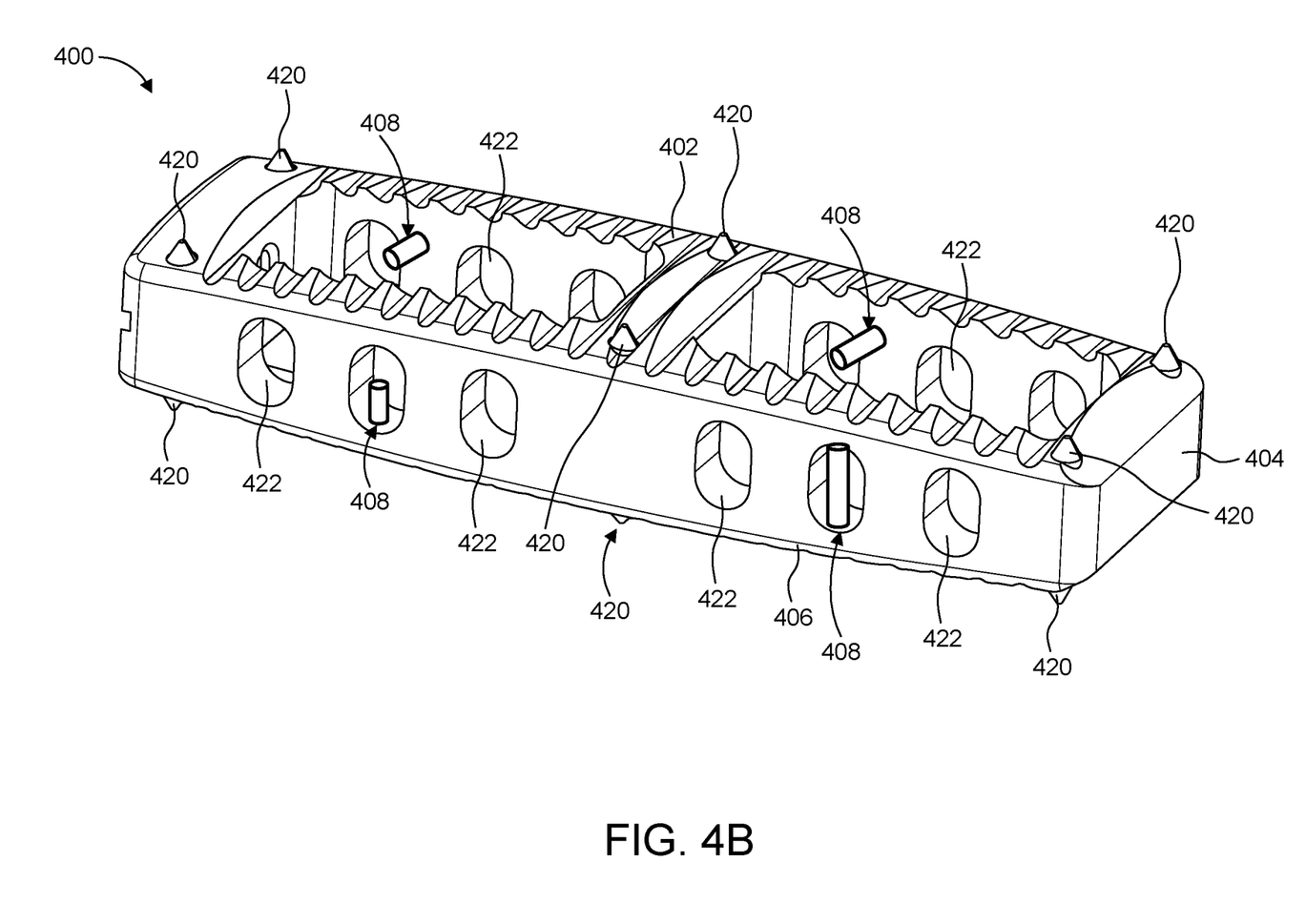
FIG. 4B illustrates another view of the example structure of the implant depicted in FIG. 4A and in accordance with examples of the present disclosure.

FIGS. 4A and 4B illustrate a further example structure of the implant in accordance with examples of the present disclosure. The implant 400 in FIGS. 4A 4B includes resonators 408, spikes 420, visualization apertures 422, two fusion apertures 403 separated by medial support 430, and ridges 426. The resonators 408 are shown in various positions and with assorted sizes, and the resonators 408 may be sized and/or positioned differently in other examples. Additionally, there may be more or fewer resonators 408 as required and/or desired for the application of the implant. Furthermore, the resonators 408 may be embedded in the body 404 of the implant 400 and may not be visible as shown in FIGS. 3A-B. For example, the body 404 may be made of polymer compositions (e.g., PEEK or PEKK) and the resonators 408 embedded in the body 404 may be made of Ti6Al4V.

The visualization apertures 422 may aid in visualization at the at the time of implantation and at subsequent clinical evaluations. The resonators 408 positioned at the visualization apertures 422 may be positioned and/or sized such that the visualization apertures 422 may still be used to aid in visualization. For example, the resonators 408 can be sized to be smaller than the illustrated example, but the resonators are shown at the illustrated size for clarity.

The fusion apertures 403 may allow for direct bone ossification, and the medial support 430 may provide structural support to the implant 400. The first bone contacting surface 402 and/or the second bone contacting surface 406 may comprise the ridges 426. The ridges 426 may act as anti-migration features such designed to increase the friction between the implant 400 and the adjacent contacting surfaces of the bone, e.g., the vertebral bodies, to prohibit migration of the implant 400 after implantation. The spikes 420 may also function as anti-migration features and/or act as position identifying features. For example, the implant 400 may be constructed of material that does not appear on images produced using imaging techniques such as an X-ray. Thus, constructing the spikes 420 of material that does appear on images produced using the imaging techniques causes the spikes to function as position identifying features. Additionally, the spikes 420 may be constructed to be resonators of the implant 400. For example, the spikes 420 may constructed out of a material and sized to have a specific length, diameter, etc. to resonate at a specific frequency, such as the 1.5 MHz frequency of a LIPUS wave. The resonators 408 shown in FIGS. 3A-B may be omitted in this example or implemented along with the spikes 420.

Figure 6:
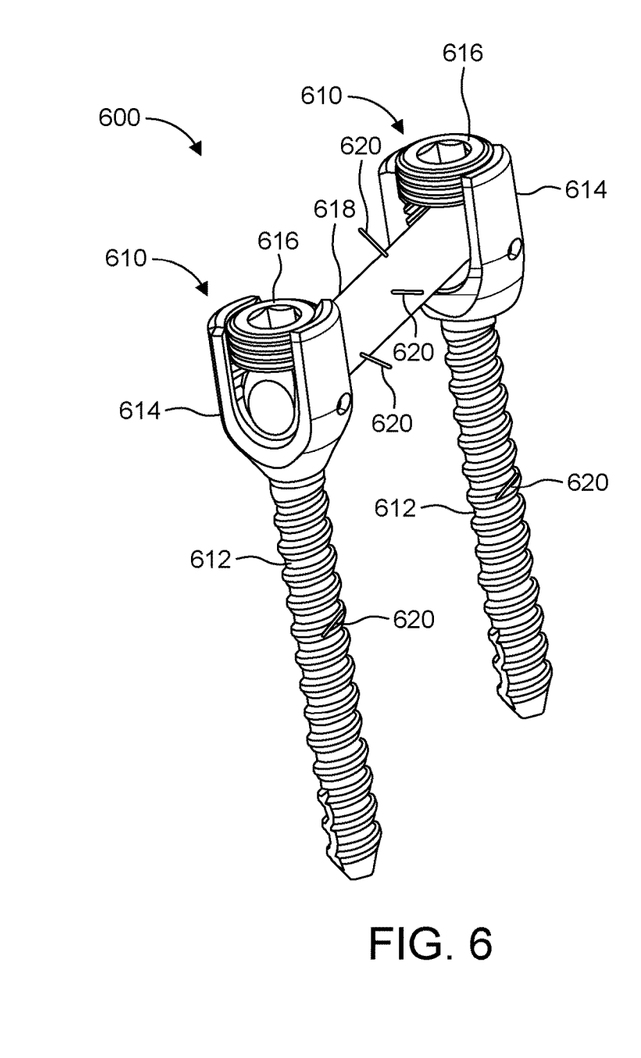
FIG. 6 illustrates a spinal fixation system benefitting from aspects disclosed herein.

FIG. 6 illustrates a spinal fixation system 600 benefitting from aspects disclosed herein. Certain of the fixation system 600 components are based on those described in U.S. Pat. No. 7,833,251 (application Ser. No. 11/031,506), filed Jan. 6, 2005, which is incorporated herein by reference in its entirety for any and all purposes, and include pedicle screw assemblies 610 and a rod 618. The pedicle screw assemblies 610 each include a screw 612, a tulip 614, and a setscrew 616. The screw 612 can be a pedicle screw integral with or couplable to the tulip 614. The tulip 614 is a component configured to receive the rod 618, which is held in place by the setscrew 616. The fixation system 600 can be improved via the inclusion of various resonators 620. As illustrated, one or more resonators 620 can be disposed on or in the screw 612 (e.g., on or in screw threads or between the threads), on the tulip 614, on the setscrew 616, on the rod 618, elsewhere, or combinations thereof. In some examples, the resonators 620 are configured to reduce an interference between the resonators 620 and other components, such as by being angled or otherwise disposed in particular ways. In some procedures, the bone graft material is placed within or along the lateral gutters of vertebrae and along the rod 618. The resonators 620 on or associated with the rod 618 or other aspects of the system 600 facilitate bone growth of the bone graft material within or along the lateral gutters.

Figure 7:
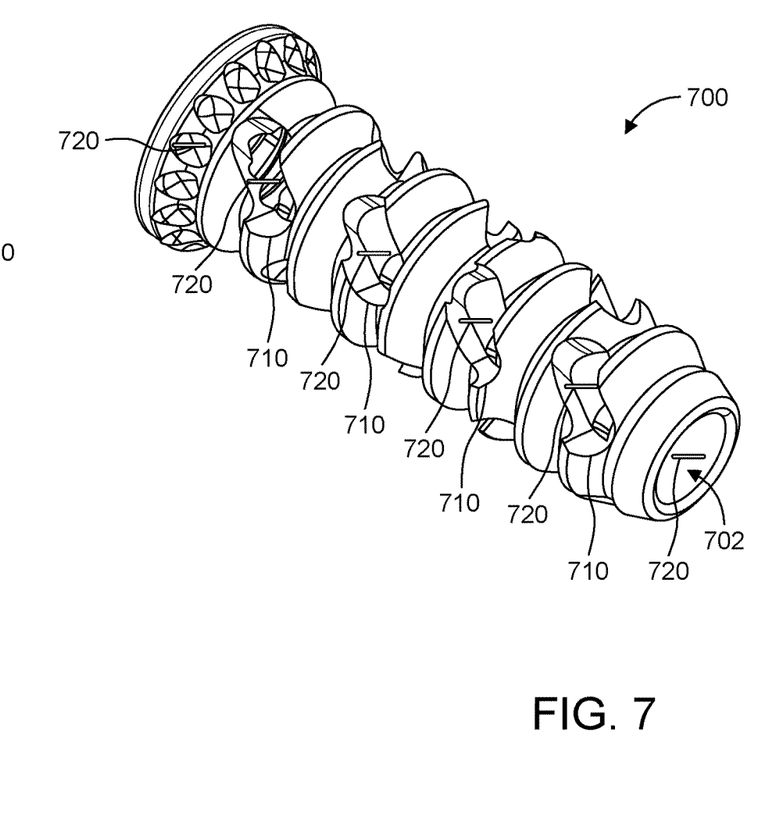
FIG. 7 illustrates a sacroiliac joint fusion implant benefitting from aspects disclosed herein.

FIG. 7 illustrates a sacroiliac joint fusion implant 700 benefitting from aspects disclosed herein. Certain features of the implant 700 are based on those described in U.S. Pat. No. 10,179,014, filed Mar. 14, 2013, which is incorporated herein by reference in its entirety for any and all purposes, and includes a through-hole 702 extending from a distal to a proximal end of the implant 700, and a plurality of fusion apertures 710, among other features. The implant 700 can benefit from the inclusion of one or more resonators 720 as described herein. For example, the resonators 720 can be disposed on or within any of the features of the implant 700. Further, one or more components of the implant 700 can be configured to resonate.

Figure 8:
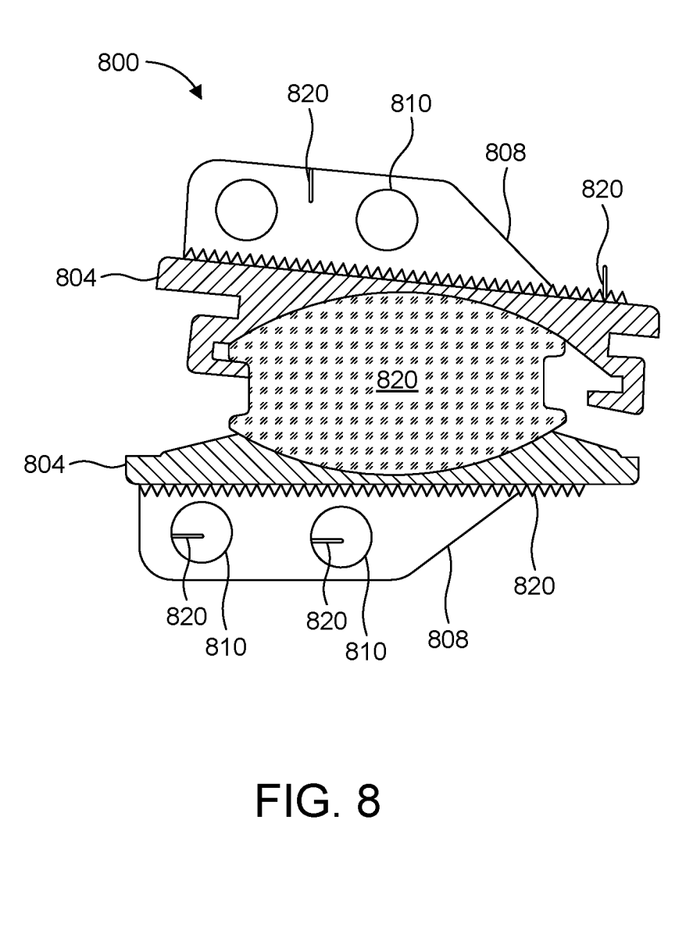
FIG. 8 illustrates a lateral partial cross sectional view of a prosthetic disc benefitting from aspects disclosed herein.

FIG. 8 illustrates a lateral partial cross sectional view of a prosthetic disc 800 benefitting from aspects disclosed herein. Certain features of the prosthetic disc 800 are based on those described in U.S. Pat. No. 9,107,762 (application Ser. No. 13/830,028), filed Nov. 3, 2011, which is incorporated herein by reference in its entirety for any and all purposes, and includes a core 802 disposed between plates 804 having serrations 806 fins 808 defining apertures 810. The implant 800 can benefit from the inclusion of one or more resonators 820 as described herein. For example, the resonators 820 can be disposed on or within any of the features of the implant 800. Further, one or more components of the implant 800 can be configured to resonate. In contrast to resonators being used with an intervertebral implant to encourage spinal fusion, the one or more resonators 820 here can be used to encourage connection between the plates 804 of the prosthetic disc 800 and adjacent bone (e.g., superior or inferior vertebral body of the cervical, thoracic, or lumbar spine). The resonators 820 include cylindrical resonators and spikes that may also provide stability to the implant and resist the implant from migrating.

Figure 9:
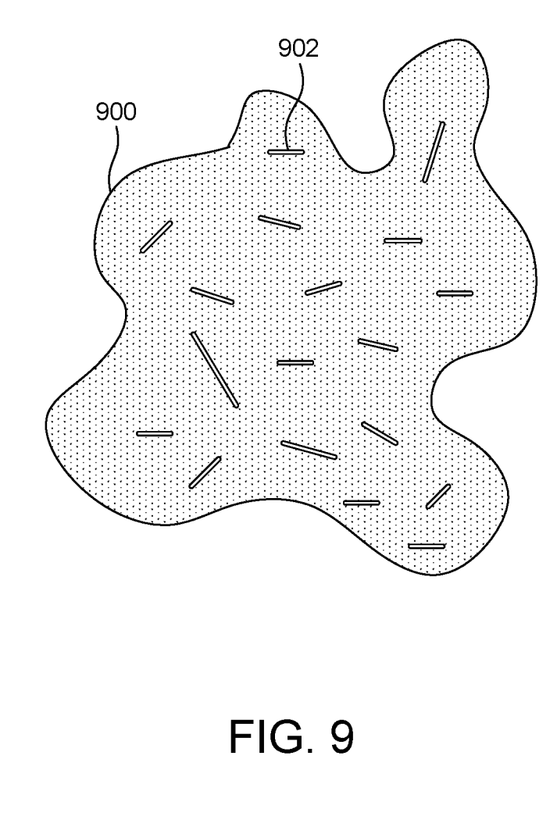
FIG. 9 illustrates a bone growth material having one or more resonators disposed therein.

FIG. 9 illustrates a bone growth material 900 having one or more resonators 902 disposed therein. The bone growth material 900 can include any of a variety of materials, such as autologous bone harvested from the patient, bone allograft, bone xenograft, any number of non-bone implants (e.g. ceramic, metallic, polymer), bone morphogenic protein, and bio-resorbable compositions, other materials, or combinations thereof. The one or more resonators 902 can be any one or more resonators described herein.

Method for Using the Resonating Interbody Implant

Figure 5:
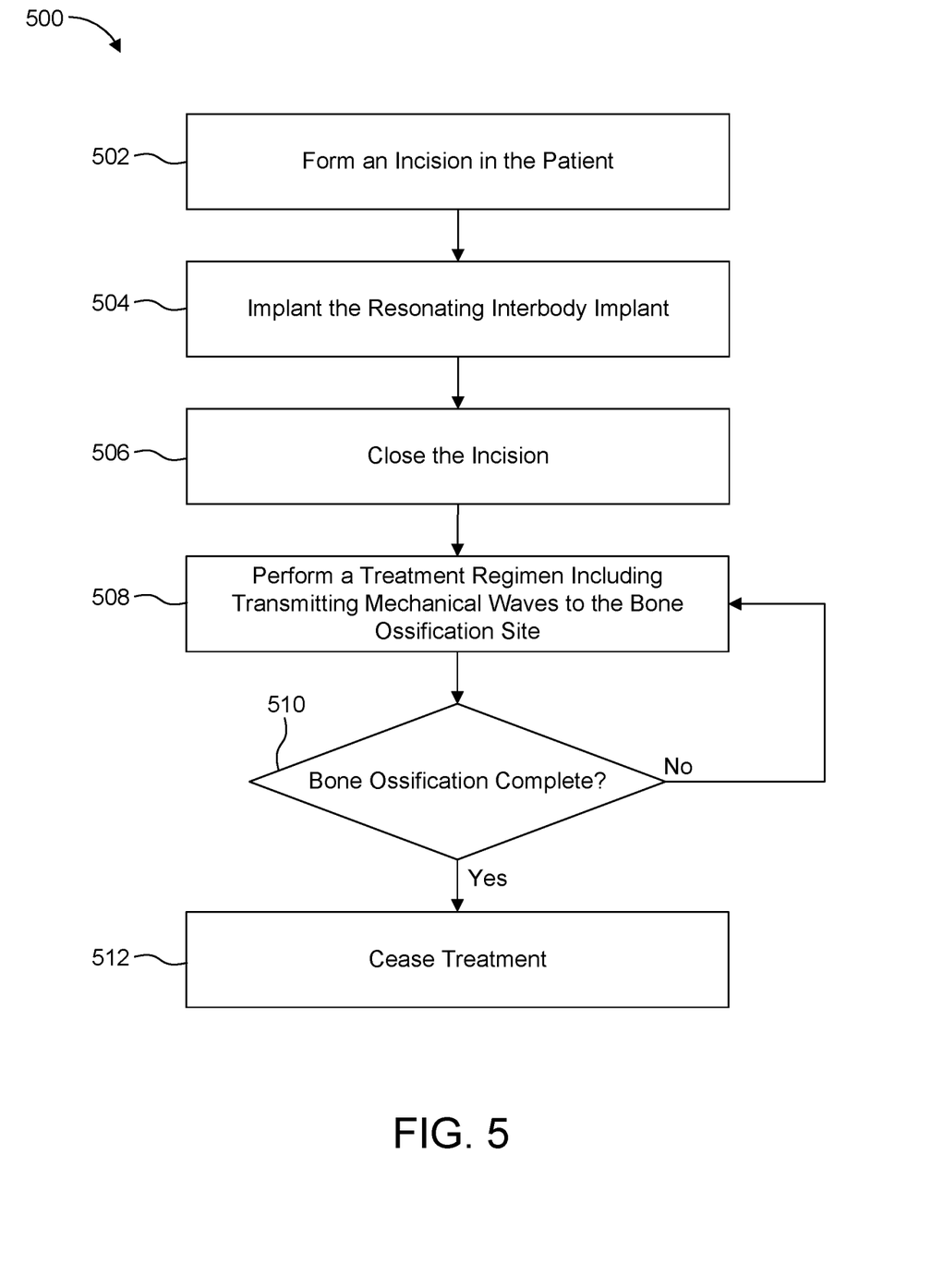
FIG. 5 illustrates a method for using the implant for bone ossification in accordance with examples of the present disclosure.

FIG. 5 illustrates a method for using the implant for bone ossification in accordance with examples of the present disclosure. Method 500 begins at operation 502. In operation 502, an incision is formed in the patient. For example, an incision is made near a site where bone ossification is to occur, and the incision is made to access the space for a resonating interbody implant to be implanted at the site. Example sites include a space between adjacent vertebrae for a spinal fusion procedure, a site between portions of bone for a bone transport procedure or a bone healing procedure, or the like. Example access techniques include anterior, lateral, transforaminal, posterior, other approaches, or combinations thereof.

Once the incision is formed in the patient, the resonating interbody implant (e.g., one of the implants 100, 200, 300, 400 described above) is implanted at the site. For example, the implant may be placed in the space between two adjacent vertebrae for accelerating bone ossification during the spinal fusion procedure. Implanting the implant may include packing the implant with bone grafting material to further promote bone formation. For example, the implant may be packed with calcium sulfate, bioactive glass, calcium phosphate, and/or some other material that can be used as bone graft material.

Once the implant is implanted, the incision is closed or allowed to close in operation 506. For example, the incision is closed by stitches, adhesive, or via some other method.

In operation 508, a treatment regimen is performed which includes transmitting mechanical waves to the bone ossification site. For example, a LIPUS system, including a wave generator, is used to transmit LIPUS waves to the bone ossification site. The wave generator can be any of a variety of devices known in the art configured to generate therapeutic waves, such as LIPUS. The implanted resonating interbody implant will resonate in response to the transmitted LIPUS waves and accelerate bone ossification. The treatment regimen may be prescribed for a period of bone ossification. The treatment regimen may include a twenty minute treatment of LIPUS wave transmission daily for a period of three to six months for example.

The treatment regimen may include using a device that positions the wave generator at the desired location for transmitting the waves. For example, the LIPUS system may include a belt or other type of fastening device that positions the wave generator to transmit waves to the implant positioned between the adjacent vertebrae. In some examples, the treatment regimen includes activating an active implanted wave generator. In other examples, the treatment regimen lacks any step of activating an implanted wave generator. In some examples, the sole source of the waves is extracorporeal.

In operation 510, it is determined whether bone ossification is complete. For example, the site where bone ossification is occurring may be evaluated, such as via an imaging technique (e.g., one or more x-ray or CT scan images) or via an implanted fusion sensor. Bone ossification may be considered complete when a fracture is healed sufficiently, when adjacent vertebrae are fused, when a bone transport procedure is complete, or the like. If it is determined that bone ossification is not complete, flow proceeds back to operation 508, and the treatment regimen is continued. In some examples, modifications to the treatment regimen may be made based on the determination in operation 510.

If it is determined that bone ossification is complete in operation 510, method 500 proceeds to operation 512, and treatment is ceased.

The foregoing disclosure of the exemplary examples of the present subject disclosure has been presented for purposes of illustration and description. The disclosure is not intended to be exhaustive or to limit the subject disclosure to the precise forms disclosed. Many variations and modifications of the examples described herein will be apparent to one of ordinary skill in the art in light of the above disclosure. The scope of the subject disclosure is to be defined only by the claims appended hereto, and by their equivalents.

Further, in describing representative examples of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular examples only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another, for example when the apparatus is right side up.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Illustrative examples of the disclosure are described herein. In the interest of clarity, not all features of an actual implementation are described in this specification. It will of course be appreciated that in the development of any such actual example, numerous implementation-specific decisions must be made to achieve the developers' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. The patient positioning systems and related methods disclosed herein boast a variety of novel features and components that warrant patent protection, both individually and in combination.

While the subject matter is susceptible to various modifications and alternative forms, specific examples thereof have been shown by way of example in the drawings and are herein described in detail. It should be understood, however, that the description herein of specific examples is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The invention claimed is:

1. A method comprising:
   implanting, in a patient, an interbody implant having a plurality of resonators between adjacent vertebrae, wherein a length of each of the resonators is configured to resonate at a predetermined frequency of an external wave generator; and
   transmitting from outside the patient, by the wave generator, mechanical waves towards the implanted interbody implant at the predetermined frequency, thereby causing the plurality of resonators to resonate at the predetermined frequency to promote bone growth.

2. The method of claim 1, wherein the mechanical waves comprise low intensity pulsed ultrasound waves.

3. The method of claim 1, wherein each mechanical wave has a pulse width of approximately two hundred microseconds, wherein the wave generator is configured to transmit the mechanical waves at least every millisecond.

4. The method of claim 1, wherein each mechanical wave has a frequency of approximately 1.5 megahertz.

5. The method of claim 1, further comprising:
   performing a treatment regimen, wherein the treatment regimen includes the transmitting;
   determining that ossification occurred in the space between the adjacent vertebrae,
   wherein the interbody implant is at least partially encapsulated by the ossification; and
   ceasing the treatment regimen responsive to the determining.

6. The method of claim 1, further comprising packing the interbody implant with bone graft material.

7. The method of claim 1, further comprising:
   prior to implanting the interbody implant, forming an incision in a patient having the adjacent vertebrae to access the space;
   after implanting the interbody implant, closing the incision; and
   wherein the transmitting occurs after closing the incision.

8. The method of claim 1, wherein at least a portion of the plurality of resonators are spikes positioned to directly contact a bone when the implant is implanted.

9. An intervertebral implant, comprising:
   a first bone contacting surface;
   a second bone contacting surface;
   a body defined between the first and second bone contacting surfaces, and adapted to be implanted into a patient; and
   a plurality of resonators at any one of (i) the first bone contacting surface, (ii) the second bone contacting surface, (iii) the body, or (iv) any combination of (i), (ii), and (iii), wherein a length of each of the resonators is configured to resonate at a predetermined frequency of an external wave generator located outside the patient.

10. The implant of claim 9, wherein the resonators are constructed to resonate at a predetermined frequency.

11. The implant of claim 10, wherein the predetermined frequency is a frequency associated with low intensity pulsed ultrasound.

12. The implant of claim 9, wherein the resonators are affixed to a portion of the implant; and wherein the resonators comprise a cylindrical shape constructed to resonate at a predetermined frequency.

13. The implant of claim 9, wherein each resonator of the plurality of resonators comprises a first end and a second end, and wherein the resonators are affixed by any one of (i) the first end, (ii) the second end, or (iii) the first end and the second end.

14. The implant of claim 9, wherein the implant comprises poly-ether-ether-ketone.

15. The implant of claim 9, wherein the implant lacks an active component.

16. The implant of claim 9,
   wherein the first and second bone contacting surfaces are porous; and
   wherein at least a portion of the porous surfaces of the first and second bone contacting surfaces are constructed to resonate at a predetermined frequency.

17. The implant of claim 9, wherein the implant is a total disc replacement implant.

18. The implant of claim 9,
   wherein the body is porous, the porous body comprising a porous lattice structure; and
   wherein the porous lattice structure is configured to resonate at a predetermined frequency.

19. The implant of claim 9, wherein the body and the first and second bone contacting surfaces are porous, the porous body comprising a lattice structure, wherein the porous lattice structure and the porous surfaces of the first and second bone contacting surfaces are configured to resonate at a predetermined frequency.

20. The implant of claim 9, wherein the resonators are constructed to resonate in response to receiving a mechanical wave with:
   a frequency of approximately 1.5 megahertz;
   an intensity of less than 0.1 Watts per meter squared; and
   a pulse width of approximately two hundred microseconds.

21. The implant of claim 9, wherein at least a portion of the plurality of resonators are spikes positioned to directly contact a bone when the implant is implanted, thereby providing stability to the implant.

* * * * *